(12) United States Patent
Cantor et al.

(10) Patent No.: US 7,166,437 B2
(45) Date of Patent: Jan. 23, 2007

(54) MEASUREMENT OF ELASTIC FIBER BREAKDOWN PRODUCTS IN SPUTUM

(76) Inventors: Jerome Owen Cantor, 242 92nd St., Brooklyn, NY (US) 11209; Bronislava Shteyngart, 242 92nd St., Brooklyn, NY (US) 11209

( * ) Notice: Subject to any disclaimer, the term of this patent is extended or adjusted under 35 U.S.C. 154(b) by 471 days.

(21) Appl. No.: 10/253,756

(22) Filed: Sep. 24, 2002

(65) Prior Publication Data

US 2004/0058382 A1    Mar. 25, 2004

(51) Int. Cl.
 *G01N 33/53*   (2006.01)
 *G01N 33/537*  (2006.01)
 *G01N 30/90*   (2006.01)
 *G01N 24/00*   (2006.01)
 *G01N 33/557*  (2006.01)
 *G01N 33/543*  (2006.01)
 *C12N 9/00*    (2006.01)

(52) U.S. Cl. .............. 435/7.1; 435/7.92; 435/183; 436/162; 436/173; 436/517; 436/518

(58) Field of Classification Search .......... 435/7.1, 435/7.92, 183; 436/162, 173, 174, 518, 517
See application file for complete search history.

(56) References Cited

U.S. PATENT DOCUMENTS

| | | | | |
|---|---|---|---|---|
| 4,297,276 A | * | 10/1981 | Goldstein et al. | 530/324 |
| 5,217,903 A | * | 6/1993 | Stone et al. | 436/57 |
| 5,354,662 A | * | 10/1994 | Stone et al. | 435/7.92 |
| 5,633,033 A | * | 5/1997 | Nishitani et al. | 427/8 |

OTHER PUBLICATIONS

Cantor et et, Measurement of cross-linked synthesis in bleomycin-induced pulmomary fibrosis using a highly sensitive assay for desmosine and isodesmosine, Nov. 22, 1983, Colege of Physicians and Surgeons, Columbia University, vol. 103, No. 3, pp. 384-2.*
Poortmans et al, The level of Zn-alpha-2-glycoprotein in normsal human vody fluids and kidney extract, J. Lab. Clin. Med., 1968, 71: 807-811.*
Houghton Mifflin Company, The American Heritage Dictionary of the English Language, Third Edition copyright (c) 1992.*
Shlaes et al, Elastin Fibers in the Sputum of Patients with Necrotizing Pneumonia, 1983, vol. 83, No. 6, pp. 885-889.*
Shlaes et al, Sputum Elastin Fibers iand the Diagnosis of Necrotizing Pneumonia, 1985, vol. 85, No. 6, pp. 763-766.*

* cited by examiner

*Primary Examiner*—Christopher R. Tate
*Assistant Examiner*—Deborah A. Davis

(57) ABSTRACT

The subject invention is directed to the measurement of elastic fiber breakdown products in human sputum obtained from patients with emphysema and other lung diseases. Measurement of elastic fiber breakdown products may be used to monitor the progression of lung disease or to assess the efficacy of a treatment for lung disease. Such breakdown products are associated with lung injury resulting from degradation of lung elastic fibers. This process may occur in emphysema and other inflammatory disease of the lung where excess amounts of elastase are secreted by inflammatory cells. The methods for measuring elastin breakdown products in certain tissue fluids (i.e. blood, urine, bronchoalveolar lavage fluid) are well known to the art but have not been previously applied to sputum samples. The use of sputum has several advantages over other fluids, including greater specificity and ease of procurement.

6 Claims, 2 Drawing Sheets

MEASUREMENT OF ELASTIC FIBER BREAKDOWN PRODUCTS IN SPUTUM

BACKGROUND

Pulmonary emphysema is a devastating disease causing progressive destruction of lung tissue, resulting in respiratory failure. The primary target of tissue injury appears to be elastic fibers. These fibers are degraded by elastases that accumulate in the lung as a result of chronic inflammation brought on by cigarette smoking, air pollutants, infections, and other factors. Since emphysema is related to elastic fiber damage, measurement of the rate of breakdown of these fibers may be useful in assessing the progression of the disease. To date, attempts to measure elastic fiber breakdown products have involved sampling of blood, urine, tracheal aspirates, and bronchoalveolar lavage fluid. The use of blood or urine is complicated by the fact that both fluids contain elastic fiber breakdown products from tissues other than the lung, including elastic fiber-rich tissues such as blood vessels and cartilage. Consequently, diseases such as arteriosclerosis or osteoarthritis may obscure the component of elastic fiber injury due to pulmonary emphysema. The use of tracheal aspirates and bronchoalveolar lavage removes this complication, but the procedure entails a significant degree of patient discomfort and is therefore unsuitable for repeated measurements.

The only source of elastic fiber breakdown products that is readily accessible and specific for lung injury is sputum. The presence of elastic fibers in the sputum of patients with necrotizing pneumonia is well-documented (1–3). However, the quantitative measurement of elastic fiber breakdown products in sputum has not been previously attempted, nor has there been any correlation between the levels of these breakdown products in sputum and degree of lung injury.

SUMMARY OF INVENTION

The subject invention is directed to the measurement of elastic fiber breakdown products in human sputum obtained from patients with emphysema and other lung diseases. Measurement of elastic fiber breakdown products may be used to monitor the progression of lung disease or to assess the efficacy of a treatment for lung disease. Such breakdown products are associated with lung injury resulting from degradation of lung elastic fibers. This process may occur in emphysema and other inflammatory diseases of the lung where excess amounts of elastase are secreted by inflammatory cells. The methods for measuring elastin breakdown products in certain tissue fluids (i.e. blood, urine, bronchoalveolar lavage fluid, and tracheal aspirates) are well known to the art but have not been previously applied to sputum samples. The use of sputum has several advantages over other fluids, including greater specificity and ease of including greater specificity and ease of procurement.

DETAILED DESCRIPTION OF INVENTION

Figure 1:
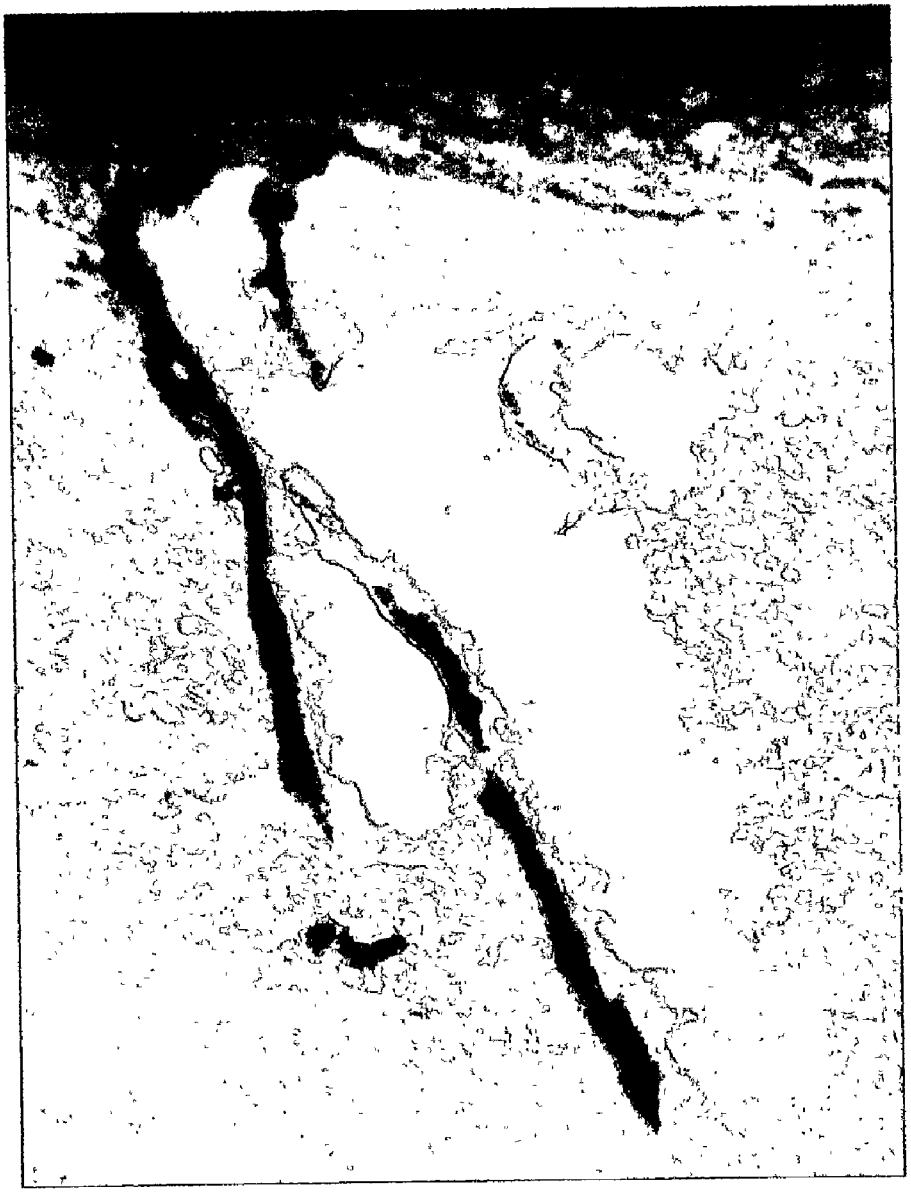
FIG. 1: Photomicrograph of elastic fiber fragments in sputum (Verhoef-Van Gieson stain).

The subject invention is directed to the measurement of elastic fiber breakdown products in human sputum obtained from patients with emphysema and other lung diseases. Measurement of elastic fiber breakdown products may be used to monitor the progression of lung disease or to assess the efficacy of a treatment for lung disease. Such breakdown products are associated with lung injury resulting from degradation of lung elastic fibers. This process may occur in emphysema and other inflammatory diseases of the lung where excess amounts of elastase are secreted by inflammatory cells. The methods for measuring elastin breakdown products in certain tissue fluids (i.e. blood, urine, bronchoalveolar lavage fluid) are well known to the art but have not been previously applied to sputum samples. The use of sputum has several advantages over other fluids, including greater specificity and ease of procurement. The following protocol incorporates the preferred embodiment of the subject invention.

Sputum samples collected from patients with emphysema and other inflammatory lung diseases are chemically degraded to separate the component amino acids of elastic fibers and other proteins. This procedure may involve hydrolyzing the sample with an acid such as HCl or a base such as NaOH, according to procedures well known to the art. The resulting hydrolysate is then measured for total elastin-specific amino acids, desmosine and isodesmosine, using paper chromatography, wherein the sputum hydrolysate is absorbed onto the paper and chromatographed in a solution of butanol, glacial acetic acid, and water (4:1:1). The highly polar elastin-specific amino acids, desmosine and isodesmosine, are immobile in this solution and may therefore be easily separated from other amino acids that have mobility. Separation may be improved by drying the chromatogram and repeating the chromatographic procedure one or more times. Alternatively, isolation of desmosine and isodesmosine may be enhanced by continuous washing of the paper in the same chromatography solution. Here, the sputum sample may be absorbed onto a filter paper disk, which is then placed in a funnel and washed with this solution.

Following chromatography, the desmosine/isodesmosine residue is stained with a 1 percent solution of ninhydrin in acetone, eluted from the paper, and measured for light absorbance at 570 nm with a spectrophotometer. The amount of desmosine/isodesmosine is quantified by comparing the amount of absorbance to standard concentrations of these amino acids. Desmosine and isodesmosine content of the sputum sample is then normalized to one or more parameters, such as total protein, albumin, or free amino acids, according to procedures well known to the art. The final value is expressed as total desmosine/isodesmosine per unit volume, protein, albumin, amino acids or other relevant parameter. Results obtained from the same patient over time may be used to determine variations in the amount of lung elastic fiber injury.

In other embodiments of the invention, desmosine and isodesmosine may be quantified by procedures involving liquid chromatography or immunoassay, according to previously published procedures (4–6). Alternatively, direct measurement of desmosine and isodesmosine in sputum hydrolysates may be performed using ultraviolet spectroscopy, fluorescence spectroscopy, mass spectroscopy, or other spectroscopic techniques well-known to the art.

EXPERIMENTAL METHODS

Sputum samples from patients with inflammatory lung disease were processed for histological evaluation. Slide sections treated with the Verhoeff-Von Gieson elastic fiber stain revealed the presence of fragmented elastic fibers (FIG. 1).

In order to quantify the amount of desmosine and isodesmosine present in the sputum, a 5-ml sample from a heavy smoker with COPD was placed in 6 N HCl and hydrolyzed at 100 degrees centigrade for 24 hrs. After addition of NaOH to normalize the pH, the hydrolysate was filtered to remove particulates, and subjected to descending paper chromatography in a system of butanol, glacial acetic acid, and water (4:1:1). The chromatogram was allowed to dry, then stained with a solution of 1 percent ninhydrin in acetone. The origin of the chromatogram, containing desmosine and isodesmosine, was eluted in alcohol and measured for absorbance at 570 nm with a spectrophotometer.

Figure 2:
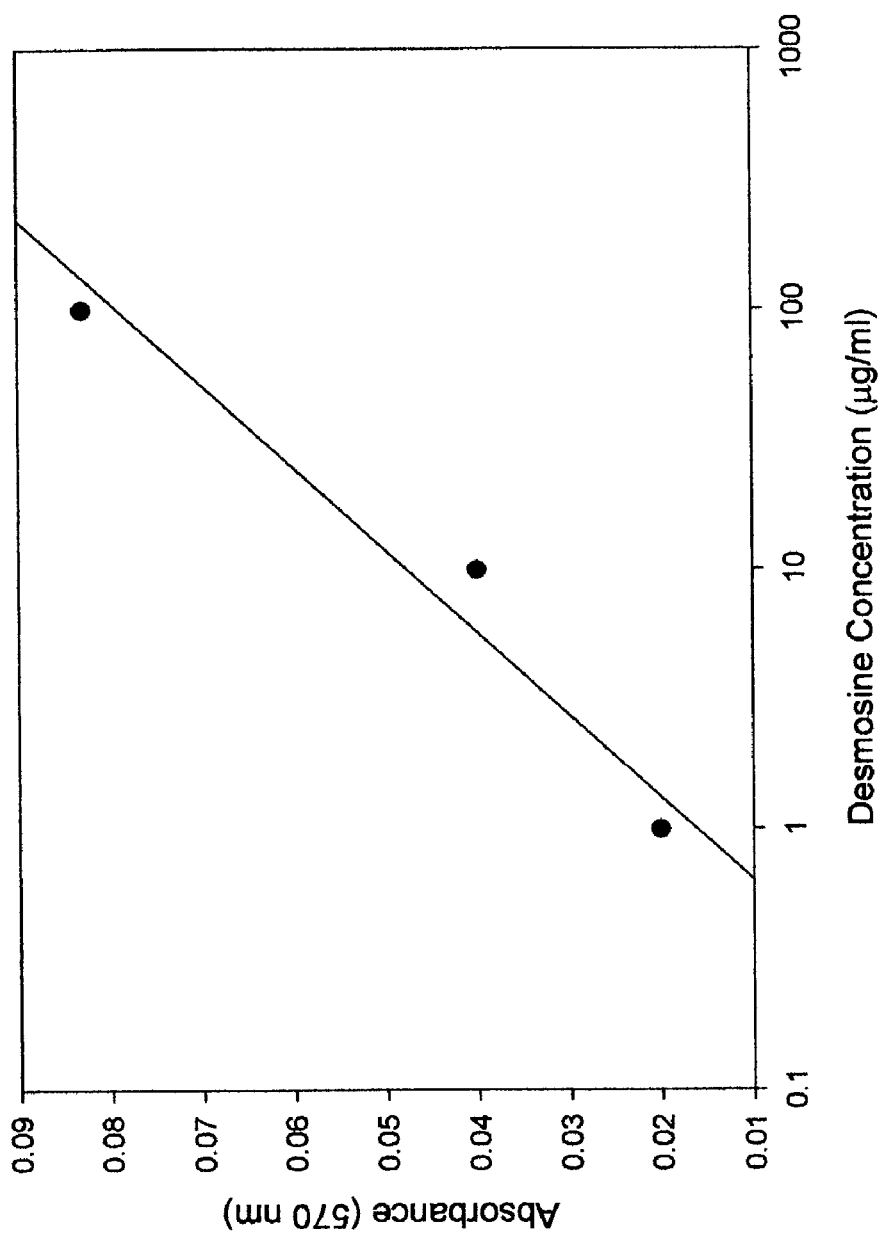
FIG. 2: Graph showing correlation between desmosine/isodesmosine concentration and light absorbance at 570 nm.

To determine the actual amount of desmosine/isodesmosine in the sample, the absorbance was compared to standard concentrations of these amino acids subjected to the same chromatographic procedure. As shown in FIG. 2, the amount of absorbance was directly proportional to concentration. Using linear regression, it was found that the sputum sample from the COPD patient contained 1.5 μg desmosine/isodesmosine per ml of fluid.

REFERENCES

1. Volkovysskaia V B, Nepomniashchikh. Staining elastic fibers in sputum. Lab Delo 1969;7:415–417.

What is claimed is:

1. A method of determining lung injury in a mammal due to pulmonary emphysema, asthma, bronchitis, respiratory distress syndrome, cystic fibrosis, or interstitial pulmonary fibrosis, comprising measurement of desmosine and isodesmosine in sputum.

2. A method of claim 1, wherein the mammal is a human.

3. A method of claim 1, wherein measurement of desmosine and isodesmosine comprises hydrolysis in the sputum, follow by paper chromatography in a composition comprising butanol, glacial acetic acid, and water (4:1:1).

4. A method of claim 1, wherein measurement of desmosine and isodesmosine comprises a separation procedure other than paper chromatography, whereby the separation procedure comprises liquid chromatography, high-performance liquid chromatography, thin-layer chromatography, or electrophoresis.

5. A method of claim 1, wherein measurement of desmosine and isodesmosine comprises employing an immunoassay.

6. A method of claim 1, wherein measurement of desmosine and isodesmosine comprises employing spectroscopy, including mass spectrometry, fluorescence spectrometry, ultraviolet spectrometry, infrared spectrometry, ultraviolet spectrometry, infrared spectrometry, and visible wavelength spectrometry.

* * * * *